United States Patent [19]

Revici

[11] 4,368,206

[45] Jan. 11, 1983

[54] METHOD FOR TREATING ALCOHOLISM AND ELIMINATING AND PREVENTING ALCOHOL INTOXICATION

[76] Inventor: Emanuel Revici, 1111 Park Ave., New York, N.Y. 10028

[21] Appl. No.: 106,129

[22] Filed: Dec. 21, 1979

Related U.S. Application Data

[63] Continuation-in-part of Ser. No. 917,956, Jun. 22, 1978, abandoned, which is a continuation of Ser. No. 724,367, Sep. 17, 1976, abandoned, which is a continuation-in-part of Ser. No. 546,712, Feb. 3, 1975, abandoned, which is a continuation-in-part of Ser. No. 450,169, Mar. 11, 1974, abandoned.

[51] Int. Cl.$^3$ ............................................. A61K 31/23
[52] U.S. Cl. .................................... 424/312; 424/164; 424/165; 260/399
[58] Field of Search .................. 424/95, 164, 165, 312; 260/399

[56] References Cited

U.S. PATENT DOCUMENTS

| | | | |
|---|---|---|---|
| 774,224 | 11/1904 | Winternitz | 424/312 |
| 1,368,974 | 2/1921 | Serghison | 424/312 X |
| 1,516,562 | 10/1924 | Calabro | 424/312 X |
| 2,083,572 | 6/1937 | McKee | 424/312 X |
| 2,114,370 | 4/1938 | Bickenheuser | 424/312 X |
| 2,567,814 | 9/1951 | Jacobsen et al. | 424/328 |
| 2,647,145 | 7/1953 | Hald et al. | 260/157 |
| 2,799,619 | 7/1957 | Seifter et al. | 424/174 |
| 2,819,199 | 1/1958 | Kalish | 424/312 |
| 2,853,419 | 9/1958 | Degkwitz | 424/312 |
| 2,998,350 | 8/1961 | De Gruniger et al. | 424/129 |
| 4,144,348 | 3/1979 | Pyatnitskaya et al. | 424/274 |
| 4,153,700 | 5/1979 | Rosenberg | 424/261 |
| 4,156,013 | 5/1979 | Bruinvels et al. | 424/319 |

FOREIGN PATENT DOCUMENTS

1077378 7/1967 United Kingdom .

OTHER PUBLICATIONS

Chemical Abstracts 83:189123v (1975), (Abst. of Ger. Offen. 2510038).
Revici, Research in Physiopathy, pp. 334-336, (1961).
U.S. Pharmacopeia, 18th Revision, p. 601, (1970).
Ralston, Fatty Acids and Their Derivatives, p. 465, (Wiley), 1948.
Taranenko, Zhurnal Prikladnoi Khimii, 33, 1203-1207, (1960).
Hotten-Sulfurized Sperm Whale Oil, in NGLI Spokesman, 174-178, (1973).
Hirabayashi et al., Agricultural Chem. (Japan), vol. 4, 1959.
Pryor, Mechanisms of Sulfur Reactions, pp. 42-45 & 57-116, (1962).

*Primary Examiner*—Leonard Schenkman
*Attorney, Agent, or Firm*—Millen & White

[57] ABSTRACT

The invention relates to a method of treating alcoholism and for aiding in controlling alcohol intoxication in humans by the internal administration of a composition produced by heating certain allylically unsaturated compounds sufficient to substantially increase the peroxide titer. The incorporation of sulfur in the composition during the heating has been found to be particularly advantageous.

25 Claims, No Drawings

METHOD FOR TREATING ALCOHOLISM AND ELIMINATING AND PREVENTING ALCOHOL INTOXICATION

CROSS-REFERENCE TO RELATED APPLICATIONS

This application is a continuation-in-part of application Ser. No. 917,956, filed June 22, 1978, now abandoned, which in turn is continuation of application Ser. No. 724,367, filed Sept. 17, 1976, now abandoned, which in turn is a continuation-in-part of application Ser. No. 546,712, filed Feb. 3, 1975, now abandoned, which in turn is a continuation-in-part of application Ser. No. 450,169, filed Mar. 11, 1974, now abandoned.

BACKGROUND OF THE INVENTION

There has been much recent interest in the study of alcoholism involving biological, psychological, and sociological investigations. Publications such as the various "Proceedings of the . . . Annual Alcoholism Conference" and "Recent Advances in Studies of Alcoholism", obtainable from the Superintendent of Documents, U.S. Government Printing Office, Washington, D.C. 20402, indicate the rather intensive scientific investigations in this area. Some of these studies are concerned with the effect on a host produced by certain chemicals in combination with alcohol.

An article by E. B. Truitt and M. J. Walsh appearing at p. 100 et sequa of "Proceedings of the First Annual Alcoholism Conference of the National Institute on Alcohol Abuse and Alcoholism", DHEW Publication No. (NIH) 74-675 (1973) discloses a number of chemicals and drugs which have been reported to have anti-alcohol effects. Included in this list are disulfiram (tetraethylthiuram disulfide—see also U.S. Pat. No. 2,567,814 Jacobsen et al), calcium carbimide (see also U.S. Pat. No. 2,998,350 de Grunigen et al), and thiocyanates which are used specifically for their anti-alcohol properties.

U.S. Pat. No. 3,860,719 Marshall discloses the use of 2-[(3,4-dichlorophenoxy)methyl]-2-imidazoline hydrochloride (fenmetozole HCl) for combating ethanol intoxication in mammals.

However, an article by H. B. McNamee et al "Fenmetozole in Acute Alcohol Intoxication in Man", *Clinical Pharmacology and Therapeutics* Vol. 17, Number 6, pp. 735-737 concludes that, within the scope of the subject study, fenmetozole does not antagonize or significantly modify acute effects of alcohol intoxication in humans.

Another publication entitled "Testing For a 'Sobering Pill'" DOT HS-801 288 (1974) available from National Technical Information Service, Springfield, Va. 22151 discloses that nikethamide, propranolol, L-dopa, pipradrol, aminophylline, ephedrine, sted-eze, and ammonium chloride were investigated to determine their potential for blocking or neutralizing the effect of alcohol on a human brain; the most effective amethystic agent found was L-dopa.

J. L. Mottin, in an article entitled "Drug-Induced Attenuation of Alcohol Consumption" *Quart. J. Stud. Alc.* 34: 444-472 (1973) discussed, inter alia, the use of the following compounds re the subject title: disulfiram, citrated calcium cyanamide, and metronidazole.

Russian Inventor's Certificate 187250 discloses the use of the "thiolic" preparations—"unitol" and "dicaptol"—for use in treating alcoholism. The Merck Index (Eighth Edition) discloses that Dicaptol (BAL or British Anti-Lewisite) is 2,3-dimercaptopropanol and is marketed as a 10% solution in peanut oil with 20% benzyl benzoate. It is further asserted that in the U.S.S.R. a water soluble form is available under the name Unithiol or Unitiol and is 2,3-dimercapto-1-propanol sodium sulfonate.

U.S. Pat. No. 2,799,619 Seifter et al. discloses compositions comprising certain phenothiazines as effective for treatment of alcoholics while British Pat. No. 1,399,992 (Revici) discloses that compositions comprising certain organic ethers are useful for the treatment of alcoholism.

SUMMARY OF THE INVENTION

The invention relates to a method for treating the manifestations of alcoholism or alcohol intoxication by aiding in the control of the craving for alcohol, or by aiding in the control of alcohol withdrawal symptoms, or by aiding in the control of alcohol intoxication in a human, which comprises internally administering to a human in need thereof an oxidized composition produced by the process comprising oxidizing, at a temperature of between about 110° C. and about 150° C., a liquid composition containing at least one fatty acid or fatty ester having allylic unsaturation of the type

and/or

for a period of time sufficient to produce a peroxide titer substantially greater than that of the untreated compound, in a non-toxic amount sufficient to aid in the control of the craving for alcohol, or to aid in the control of alcohol withdrawal symptoms, or to aid in the control of alcohol intoxication in said person. The incorporation of sulfur into the composition during or before the heating of the compositions has been found to be particularly advantageous and represents the most effective composition found to date. The compositions can be administered to the patient by the various accepted methods of injection or orally in tablet or capsule form.

DETAILED DESCRIPTION OF THE INVENTION

It is desirable to have a method for treating or aiding in the treatment of alcoholism in a human by controlling the craving for alcohol, by controlling withdrawal symptoms, or by aiding in the control of alcohol intoxication in humans. It is further desirable to have a method for aiding the control of alcohol intoxication of a non-alcoholic person by reducing or eliminating the alcohol intoxication either before or after the intake of alcohol.

This invention relates to such methods of treatment involving the internal administration to a human host of a composition produced by oxidizing a liquid composition containing a fatty acid or fatty ester, structurally characterized by allylic unsaturation, for example, by bubbling air through the reaction mixture. The fatty acid or ester advantageously includes elemental sulfur and/or a conventional free radical initiator such as tertiary-butyl peroxide during the heating step.

The allylically unsaturated compound is preferably a naturally occurring oil, containing polyunsaturated fatty esters such as an animal, vegetable, or fish oil, especially a polyunsaturated vegetable oil. Sesame oil is a vegetable oil consisting largely of triglycerides and is the most advantageous composition found to date in the practice of this invention.

The composition utilized preferably should contain a significant percentage of molecular species having allylic moieties to render the compositions useful according to the invention indicated by the following partial structures

and/or

As indicated, the unsaturation can be conjugated or nonconjugated but the composition must contain allylic methylene hydrogen.

Such compositions, as the case may be, should be oxidized or heated in the presence of oxygen at a temperature in the range between about 110° C. and about 150° C. The oxygen can be obtained by merely heating the composition open to the atmosphere but preferably and advantageously, the source of oxygen is a gas such as air injected into a heated oil such as sesame oil. The injected air also serves as a source of agitation.

As previously stated it is most advantageous to add elemental sulfur such as sublimed, precipitated, or washed sulfur to the compositions so that the sulfur is present with oxygen during at least a portion of the heating period and the sulfur incorporated into the composition. Additionally, a previous batch of the oxidized oil with or without sulfur or any commonly known and available free radical initiator, such as tert-butyl peroxide, may advantageously be present during at least a portion of the heating period.

If sulfur is added to the selected composition, for example, sesame oil, the temperature should be maintained at an upper limit within the range of about 120° C. to about 130° C., and preferably 125° C. and 127° C. These temperature limitations are based on a heating time of about one-half hour. The temperatures can be altered within limits depending on the time of heating. For example, the temperature can be 129°–130° C. if the time is shorter or even at 140° C. for very short period of time. High temperatures for a prolonged period of time tend to degrade the composition and should thus be avoided.

If sulfur is not present during the heating period, the temperature should be maintained in the range between about 110° C. and about 150° C., and preferably in the range between about 120° C. and about 140° C.

The heat treatment is conducted for a period of from about 15 minutes to about two hours. If sulfur is present, optimal results are obtained if the heat treatment is conducted for a period of time between about 30 minutes to about 1 hour. If a free radical initiator is present, or if a selected composition inherently contains a significant amount of initiator, the heat treatment period may be conducted for a relatively shorter period of time.

The precise nature of the composition which results from the above-described treatment or the identity of the effective component or components is not presently known to the Applicant. However, while Applicant does not wish his invention limited by the following theory or fact, or mixed theory and fact as the case may be, certain evidence is available which indicates that an efficacious composition for the treatment of alcoholism or the control of intoxication in a human can be produced according to this invention.

In particular, it appears that a correlation exists between a composition useful for the subject purpose and its presumed peroxide or hydroperoxide content. By adhering to the process according to this invention, it has been found that efficacious compositions are produced which yield a significant peroxide titer when monitored by conventional iodometric analysis, the results being expressed, for example, in terms of microequivalents per gram or milliequivalents per kilogram. By significant peroxide titer is meant a value obtained which is greater than that which inherently may be present in the initial untreated compound.

In the case of triglycerides which contain the allylic type unsaturation as described above, the resulting oxidized species is thought to be a hydroperoxide represented by the following partial structure

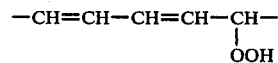

as interpreted via UV spectroscopic analysis, inter alia.

The data of Examples 3 and 4 below are consistent with the foregoing hypothesis. Trilinolein, the triglyceride of linoleic acid (9,12-octadecadienoic acid), the principal diunsaturated fatty ester in sesame oil, is subjected to the preferred treatment with air and sulfur. The resultant product has a number of properties characteristic of comparably treated sesame oil. Furthermore, its action mimics that of the treated sesame oil product in a primate model. Trilinolein is typical of a polyunsaturated oil, as is sesame oil, which contains about 35–47% linoleic acid residues in the total triglycerides.

Whatever the nature of the oxidized species, it appears amenable to monitoring by conventional iodometric analysis with or without the addition of sulfur.

Although it appears that the activity of the composition is coincident with the presence of peroxides or hydroperoxides, the efficacious agent need not necessarily be directly derived from these classes. It may in fact be those species derived from radicals resulting from decomposition of compounds of this class and may involve reaction with other molecules of, for example, triglyceride oils or sulfur including olefinic polymerization products and/or lower molecular weight decomposition products of the oils or additional products with sulfur such as sulfides, disulfides, hydropersulfides, etc.

With regard to a preferred embodiment, it appears that the presence of elemental sulfur (approximately 1% by weight based on sesame seed oil) during the oxidation of sesame seed oil acts to increase the amounts of oxidation products (conjugated hydroperoxides, diene, triene, unsaturated carbonyl) and that this increase appears optimal near 127° C. as evidenced by UV spectroscopic analysis studies. In the absence of sulfur, it appears that the region near 137° C. is optimal for the production of oxidation products.

As mentioned above, it appears that the most effective compositions are those which have a relatively high peroxide titer. Comparisons of preferred compositions, namely sesame seed oil or other polyunsaturated oils treated with air in the presence of sulfur, with other triglycerides, or triglyceride containing oils, including corn oil, cottonseed oil, and triolein with regard to their respective peroxide titers indicates a trend in peroxide levels concordant with observed bioactivity in alcoholics. Such trend of bioactivity agrees in general with the results of a peroxide analysis involving the above-identified oils in their untreated state and when oxidized in the presence of elemental sulfur under similar conditions as follows:

| Oil Used (Peroxide Analysis) | "A" Oil Saturated With Sulfur | "B" Oil Treated* With Sulfur and Air | Δ = "B − A" Difference In Peroxide |
|---|---|---|---|
| Sesame Seed (10.2) | 18.8 | 35.7 | 16.9 |
| Corn (6.8) | 11.3 | 14.9 | 3.6 |
| Cottonseed (7.3) | 10.9 | 10.2 | −0.7** |
| Olive (5.9) | 12.4 | 13.8 | 1.4 |
| Triolein (7.2) | 8.6 | 8.5 | −0.1** |

*Heated at 127° C. for 0.50 hrs. with 90 l/min. air addition and rapid mechanical stirring and containing 1.0% elemental sulfur by weight.
**Within experimental error.

It is thought that a lower bioactivity and a lower peroxide titer of cottonseed oil is due to the presence of natural anti-oxidants. The elimination of the anti-oxidants from oils such as corn and cottonseed oil or the use of the relatively pure allylically unsaturated compounds or mixtures thereof will result in a substantially increased peroxide titer when treated according to this invention. Triolein contains only oleic acid moieties which are characterized by the allylically unsaturated group —CH=CH—CH$_2$— and hence is quite difficult to oxidize,* particularly when compared to the preferred sesame seed oil or other polyunsaturated oils. A peroxide titer value of 35.7 meq/kg. has been attained for the sesame seed oil-sulfur-oxygen treated composition while sesame seed oil oxidized alone at 137° C. yields a value of 63.3 meq/kg. A peroxide titer value of 35.7 meq/kg [Δ=(35.7−18.8)=16.9] has been attained for the sesame seed oil-sulfur-oxygen treated composition while sesame seed oil without sulfur oxidized at 137° C. yields a value of 63.3 meq/kg [Δ=(63.3−10.2)=53.1].
*J.Sci. Fd Agric. 1975, 26, 1353-1356.

Generally a substantial increase in the peroxide titer value can be defined as Δ3 to about Δ100 in cases where sulfur is incorporated into the composition and as from about Δ3 to about Δ400 when the oil is oxidized alone, or in the absence of sulfur.

The process used for determining the peroxide titer values discussed and reported herein are determined by placing a 2 gr. sample of the composition in a flask purged with nitrogen, and adding thereto 2 ml. of concentrated acetic acid and 0.5 grams of KI. The mixture is capped to exclude air and allowed to remain in the dark for 30 minutes to complete the reaction. The side walls are then wet down with a minimum of water and approximately 1-2 ml of a 2% starch added thereto. The solution is then immediately titrated to the end point with 0.007 normal Na$_2$S$_2$O$_3$ solution. The end point is white when small amounts of peroxides are present and slightly yellow when larger amounts are present.

The compositions as prepared according to the process of this invention should be used soon after preparation as there is indication that the peroxide titer values and effectiveness of the compositions decrease upon aging.

Preferred compositions according to this invention can be prepared by adding the sulfur to the oil, such as sesame oil, and heating the mixture with agitation at a temperature not to exceed about 130° C. It is preferable or advantageous to heat the mixture between 120° and 127° C. Heating the mixture above about 130° C. for a sufficient time causes a progressive color change in the mixture and otherwise appears to be detrimental. The temperatures given above relate to the use of sulfur with sesame oil. The ranges of temperatures which can be used to produce the compositions made according to this invention may vary with the particular oil being used, but generally a temperature of 120° C., preferably 125° C. to 127° C., will be sufficient for most oils when sulfur is added.

If the oil and sulfur is heated below about 90° C., it is difficult to incorporate the sulfur into the oil by heating and stirring alone. The best results have been obtained to date by maintaining the temperature used in forming the compositions over a prolonged period of time from about 30 minutes to one hour. Stirring aids in the reaction, and experiments to date indicate that a fairly violent stirring is advantageous. The introduction of air into the mixture during the heating is also very advantageous, particularly when the mixture is not subjected to prolonged heating and is the preferred method. The stirring can be accomplished with the introduction of the air.

After the reaction has taken place, it is cooled. Sulfur crystals remaining in the bottom of the reaction vessel can easily be removed by filtration. The remaining fluid is ready for use after appropriate sterilization for injection or incorporated into capsules, such as gelatin, for oral administration.

The amount of sulfur incorporated into the oil is advantageously between about 0.1% to 2.5% by weight, based on the oil. If higher amounts of sulfur are used they generally precipitate out. There appears to be no advantage to using higher amounts of sulfur in any event since the ultimate dosage given to the patient is the criterion rather than the amount of sulfur content in the oil.

As can be observed from Example 2 below, the incorporation of the sulfur into the oil seems to be limited to about 1% by the process presently being used to produce the sulfurized unsaturated oils.

The sulfur content can be much less than about 1% if desired and smaller sulfur content is advantageous when administered by injection. Varying the amount of sulfur below about 1% incorporated in the polyunsaturated oils for oral administration only affects the number of capsules to be taken at a given time by a particular patient.

Experiments to date indicate that the optimum sulfur content for oral administrations is about 1% and by injection about 0.1% to 0.3% by weight of the sulfur based on the weight of the oil.

The dosage prescribed to a patient will, of course, vary depending upon the particular patient and the purpose for which he is being treated. For an alcoholic, for example, it is advantageous for the patient to take 5 capsules containing 1 ml of the sulfurized oil containing about 1 to 2% sulfur for the first 3 days and to take 3 to 4 capsules a day for the next 4 days. It is preferred that the patient be relatively sober when initiating the treatment. This is generally sufficient to eliminate or reduce the desire or need for alcohol. The desire or need for alcohol generally disappears from the patient within 24 hours. This single treatment may last for months. However, the patient can be given an additional supply of the encapsulated sulfur containing oil and directed to take a capsule if he feels any desire or need for alcohol.

When the sulfurized oil is used by injection, such as intramuscularly or intraperitoneally, it is advantageous to have the sulfur contained in the sulfurized oil below about 0.5% by weight, preferably between about 0.1% to 0.3% by weight, and to inject from ½ to 3 ml of this solution into the patient. Experiments to date indicate that the injection of sulfurized oil is somewhat painful when it contains above about 0.5% sulfur. Administration by injection is, of course, not necessary but it may act faster initially. Generally if a person is given the injection of the sulfurized oil, he can also be given a supply of the oral capsules and directed to take 3 to 4 capsules a day following the injection for one week.

To reduce alcohol intoxication, the patient is directed to take 2 to 5 capsules (containing 1 ml oil at 1% sulfur). The alcohol intoxication should generally disappear within about one hour.

To prevent alcohol intoxication 1 or 2 capsules (containing 1 ml oil at 1% sulfur) can be taken prior to beginning consumption of the alcohol or with the first drink.

EXAMPLE 1

A sulfurized oil was prepared by mixing 50 grams of sublimed sulfur, obtained from Fisher Scientific, with one liter of sesame oil. The mixture was heated under fairly rapid agitation by air to a temperature of about 127° C. until all of the sulfur was incorporated into the sesame oil. The reaction mixture was then cooled to room temperature, producing at the bottom of the reaction vessel a small amount of sulfur crystals. The crystals were then separated from the liquid by filtration and about half of the crystals replaced in the resulting liquid, wherein they slowly dissolved.

The resulting sulfurized oil was then incorporated into geletin capsules in the amount of 1 ml per capsule.

A 50-year old patient, B. G., reported that he had been an alcoholic for 20 years consuming up to 1/5 to ½ gallon of hard liquor a day. The patient reported that he had tried hospitalization and different treatments without success. The patient was given 5 of the above capsules the first day and directed to take 5 capsules on the second and third days and 3 capsules for each of the 4 days remaining in the week. The patient reported no desire for alcohol after the first day and felt no need or desire for alcohol thereafter. The patient reported that he was feeling exceptionally fine.

Approximately 100 human patients have been treated to date according to this invention, including alcoholics, the social drinker when inebriated as well as to patients prior to the intake of alcohol. Significant results in controlling the craving for alcohol or controlling withdrawal symptoms or aiding in the control of intoxication were observed in approximately 80 percent of the patients treated.

EXAMPLE 2

4 g. of sulfur were weighed out and placed in an Erlenmeyer flask. 200 ml of sesame oil were added; the contents were heated to 125° C. with stirring until the sulfur dissolved. The flask was removed from heat and allowed to cool to room temperature (5 hours). Sulfur crystals were filtered into a Buchner funnel, washed thoroughly with hexane to remove residual oil, and weighed.

The above example was repeated three times. The washed sulfur precipitate was weighed in each trial and the amount of sulfur in the sesame oil calculated by difference as follows:

Initial weight of sulfur: 4.00 g
Weight of sulfur ppt.:
   Trial 1  2.05 g
   Trial 2  2.00 g
   Trial 3  1.92 g
% (w/v) sulfur in sesame oil:
   Trial 1  1.02%
   Trial 2  1.00%
   Trial 3  0.96%
   Average  0.99%

From this it was concluded that the solutions contained approximately 1% sulfur after filtration.

EXAMPLE 3

The preparation of Example 1 was repeated, except that trilinolein was substituted for sesame oil. The resultant product was significantly darker than the product of Example 1. A comparison of various properties of the oxidized, sulfurized trilinolein (OSTL) of this example with the oxidized, sulfurized sesame oil (OSSO) of Example 1 is shown in Table 1.

TABLE 1

| Property | OSTL | OSSO |
|---|---|---|
| Peroxide No. ($\mu$eq/g) | 60.9 | 55 |
| Dissolved Sulfur (%) | 1.2 | 0.75 |
| pH | 4.8 | 6.7 |
| Refractive Index ($_{20}n_D$) | 1.4831 | 1.4709 |
| UV Absorption at 254 nm. | Significantly higher than OSSO | Higher than untreated oil |
| FTIR Difference Spectrum* | Doublet at 940–990 cm$^{-1}$ | Doublet at 940–990 cm$^{-1}$ |

*Fourier Transform Infrared Difference Spectrum, permitting identification of absorption peaks in the product not present in the spectrum of the starting material.

EXAMPLE 4

The oxidized, sulfurized sesame oil (OSSO) of Example 1 and the oxidized, sulfurized trilinolein (OSTL) of Example 3 were each tested for their efficacy in alleviating alcohol withdrawal symptoms in an alcohol-addicted monkey, using untreated sesame oil as a placebo. In each case, a monkey was addicted to ethyl alcohol by infusion of 5 ml/hr for 28 days of a solution ranging between 15 and 30% ethyl alcohol in normal saline. The ethyl alcohol solution was administered via an indwelling silastic catheter implanted into the jugular vein. The presence of and severity of withdrawal was evaluated according to the presence and severity of specific symptoms, which are known to be exhibited by rhesus monkeys upon removal of alcohol in a dependent animal. Evaluation was based on a scale of 0: symptom not present, 1: mild presence of symptom, 2: moderate presence of symptom, and 3: severe presence of symptom. The symptoms evaluated were: generalized tremors, muscle fasciculations, elicited hyperreflexia, spasticity, rigidity, spontaneous hyperreflexia, fright, salivation, mydriasis, retching-vomiting, convulsive poses, convulsions, aggression, nervousness, excitability, and evoked threat.

During the 5-day placebo withdrawal period, which immediately followed the 28-day addiction period, the monkey received 5 ml of sesame oil injected into orange slices. The withdrawal symptoms were evaluated daily during this period. At the conclusion of the placebo withdrawal period, the animal was re-addicted to the ethyl alcohol over a 14-day period as described above. This was immediately followed by a 5-day drug withdrawal period. During this period, the animal received a daily dose of 5 ml of either OSTL or OSSO injected into orange slices and the daily withdrawal symptoms were evaluated. The results are shown in Table 2, where the lower the score, the less severe the symptoms and the more efficacious the therapeutic effect compared to placebo administration.

TABLE 2

Monkey Alcohol Withdrawal Scores

| Test | Treatment | Daily Withdrawal Score* | | | | | Total Score |
|---|---|---|---|---|---|---|---|
| | | 1 | 2 | 3 | 4 | 5 | |
| 1 | Placebo | 9 | 12 | 10 | 10 | 10 | 51 |
| 1 | OSTL (% Reduction**) | 8(89) | 6(50) | 4(40) | 4(40) | 4(40) | 26(51) |
| 2 | Placebo | 8 | 10 | 10 | 10 | 10 | 48 |
| 2 | OSSO (% Reduction**) | 4(50) | 4(40) | 3(30) | 3(30) | 3(30) | 17(35) |

*Using rating instrument described above.
** $\frac{Drug}{Placebo} \times 100$

It can be seen from the data of Examples 3 and 4 that both the properties and the behavior of oxidized, sulfurized trilinolein and of oxidized, sulfurized sesame oil are quite similar, and show a similar ability to alleviate the symptoms of alcohol withdrawal in a reliable primate model.

The invention also includes the use of selenium in place of elemental sulfur and for the same use. When using selenium it is combined with the allylic moiety in the same manner as sulfur but heated to a temperature in the range of 230° to 250° C., preferably about 240° C. from 15 minutes to an hour or more until the peroxide titer value is substantially greater than that of the untreated allylic moiety in the same manner as disclosed herein with respect to the use of sulfur. These compositions into which selenium is incorporated have to date not indicated as good an effect as those compositions into which sulfur is incorporated.

I claim:

1. A method for treating the manifestations of alcoholism or alcohol intoxication by aiding in the control of the craving for alcohol, or by aiding in the control of alcohol withdrawal symptoms, or by aiding in the control of alcohol intoxication in a human, which comprises internally administering to a human in need thereof an oxidized composition produced by the process comprising oxidizing, at a temperature of between about 110° C. and about 150° C., a liquid composition containing at least one fatty acid or fatty ester having allylic unsaturation of the type

and/or

for a period of time sufficient to produce a peroxide titer substantially greater than the peroxide titer of the liquid composition prior to oxidation, in a non-toxic amount sufficient to aid in the control of the craving for alcohol, or to aid in the control of alcohol withdrawal symptoms, or to aid in the control of alcohol intoxication in said person.

2. The method of claim 1, wherein the oxidation is effected by heating the liquid composition while contacting the liquid composition with air or oxygen.

3. The method of claim 1, wherein the oxidation is effected in the presence of a free radical initiator.

4. The method of claim 1, wherein the oxidation is effected in the presence of elemental sulfur, whereby an oxidized, sulfurized composition is produced.

5. The method of claim 4, wherein air or oxygen is injected into the liquid composition during the heating thereof.

6. The method of claim 5, wherein the heating is effected at a temperature of from about 120° C. to about 130° C. for from about 0.5 to about 1 hour.

7. The method of claim 1, wherein the liquid composition is an animal, vegetable or fish oil.

8. The method of claim 1, wherein the liquid composition is a vegetable oil.

9. The method of claim 1, wherein the liquid composition is a polyunsaturated vegetable oil.

10. The method of claim 1, wherein the liquid composition is sesame oil.

11. The method of claim 4, wherein the liquid composition is a polyunsaturated vegetable oil.

12. The method of claim 4, wherein the liquid composition is sesame oil.

13. The method of claim 6, wherein the liquid composition is a polyunsaturated vegetable oil.

14. The method of claim 6, wherein the liquid composition is sesame oil.

15. The method of claim 6, wherein the sulfur content of the resultant oxidized, sulfurized composition is from about 0.1% to about 2.5% by weight.

16. The method of claim 15, wherein the composition is administered orally.

17. The method of claim 16, wherein the liquid composition is sesame oil.

18. The method of claim 4, wherein the sulfur content of the resultant, oxidized sulfurized composition is about 0.1% to about 0.3% by weight, and the composition is administered intramuscularly or intraperitoneally.

19. The method of claim 4, for aiding in the control of alcohol withdrawal symptoms, wherein said non-toxic amount is an amount sufficient to aid in the control of alcohol withdrawal symptoms.

20. The method of claim 19, wherein air or oxygen is injected into the liquid composition during the heating thereof.

21. The method of claim 20, wherein the heating is effected at a temperature of from about 120° C. to about 130° C. for from about 0.5 to about 1 hour.

22. The method of claim 21, wherein the liquid composition is sesame oil.

23. The method of claim 21, wherein the sulfur content of the resultant oxidized, sulfurized composition is from about 0.1% to about 2.5% by weight.

24. The method of claim 23, wherein the composition is administered orally.

25. The method of claim 24, wherein the liquid composition is sesame oil.

* * * * *